United States Patent [19]

Yamana et al.

[11] Patent Number: 5,965,496
[45] Date of Patent: Oct. 12, 1999

[54] FLUORINE-CONTAINING COMPOUNDS AND USE THEREOF

[75] Inventors: Masayuki Yamana; Yoshitaka Honda, both of Settsu, Japan

[73] Assignee: Daikin Industries, Ltd., Osaka, Japan

[21] Appl. No.: 08/817,440

[22] PCT Filed: Oct. 12, 1995

[86] PCT No.: PCT/JP95/02084

§ 371 Date: May 23, 1997

§ 102(e) Date: May 23, 1997

[87] PCT Pub. No.: WO96/11905

PCT Pub. Date: Apr. 25, 1996

[30] Foreign Application Priority Data

Oct. 13, 1994 [JP] Japan .................................. 6-248148

[51] Int. Cl.$^6$ ...................... C07C 243/00; C10M 105/56
[52] U.S. Cl. .................. 508/244; 508/255; 508/267; 508/549; 508/546; 428/695; 252/62.54; 544/179; 546/184; 546/248
[58] Field of Search ................................... 508/244, 267, 508/255, 546

[56] References Cited

U.S. PATENT DOCUMENTS

| | | | |
|---|---|---|---|
| 4,267,238 | 5/1981 | Chernega | 428/422 |
| 4,268,556 | 5/1981 | Pedrotty | 428/65 |
| 4,757,145 | 7/1988 | Caporiccio et al. | 546/81 |
| 4,912,252 | 3/1990 | Dekura et al. | 560/140 |
| 5,188,747 | 2/1993 | Kai et al. | 252/54 |
| 5,453,539 | 9/1995 | Kondo et al. | 562/586 |

OTHER PUBLICATIONS

Z. Chem., vol. 29, No. 5 pp. 175–176, 1989.

Kupfer et al, "Synthesis and ESR spectroscopy of the spin probe 4–(perfluoroctanoyloxyl)–2,2,6,6–tetramethylpiperidin–2–oxyl". Chemical Abstracts 112:76891, Jan. 1989.

Ristori et al, "Magnetic Resonance Charaterization of Betaine Micelles and Betaine–Perfluoropolyether Mixed Vesicles". Chemical Abstract 126:347614, Jan. 1997.

Primary Examiner—Ellen M. McAvoy
Attorney, Agent, or Firm—Larson & Taylor

[57] ABSTRACT

A fluorine-containing polyether compound, a lubricant, and a magnetic recording medium comprising the lubricant.

4 Claims, No Drawings

FLUORINE-CONTAINING COMPOUNDS AND USE THEREOF

TECHNICAL FIELD

The present invention relates to a lubricant prepared by modifying terminals of fluorine-containing polyethers, perfluoroalkyl compounds or perfluoroalkenyl with organic free radicals, especially a lubricant for magnetic recording medium, and a magnetic recording medium comprising said lubricant.

The lubricant firmly adhered to a surface of base made of, in particular, carbon, amorphous carbon, graphite, ceramics, metals, etc. as a thin layer imparts improved lubricating properties to the base leading to excellent lubrication of a magnetic recording medium.

BACKGROUND ART

Improvement of magnetic recording density of magnetic recording media, such as tapes, cards, discs has been requested more and more leading to severe sliding conditions between a magnetic recording head and a magnetic face. Specifically, a decrease of distance between a magnetic recording head and a magnetic recording face, or an increase of sliding rate occurs leading to requirement of improved performance of lubricants applied to the surface of magnetic recording medium from the viewpoint of duration and utility.

Previously, for example, U.S. Pat. No. 3,715,378 discloses perfluoroethers as lubricants applied to magnetic recording media.

The perfluoropolyethers are excellent lubricants because of superior properties of heat-resistance, chemical inactivity and low vapor pressure. However, the perfluoropolyethers alone are inferior in adsorptivity to a medium which makes it difficult to employ the perfluoropolyethers by itself as a lubricant for magnetic recording medium.

Attempts of converting terminals of perfluoropolyethers into polar groups by the action of which perfluoropolyether lubricants were adhered to a base medium were carried out so as to improve an adsorptivity of the lubricants to the medium (see, U.S. Pat. No. 4,267,238; U.S. Pat. No. 4,268, 556; and Japanese Unexamined Patent Publication No. 61-4727).

Lubricants comprising perfluoroalkylpolyethers having polar groups at terminals are adhered to a medium by the action of the polar groups and maintain lubricating properties by perfluoropolyoxy-alkylene chain elongated therefrom.

However, requests for significant improvement of magnetic recording density lead to higher requests for improvement of lubricating properties of lubricant for use in magnetic recording medium. Under these circumstances, even perfluoropolyethers with polar groups are not practically enough in lubricating properties and durability.

It is an object of the invention to provide a lubricant for magnetic recording medium imparting good lubricating properties to magnetic recording medium and a fluorine-containing compound useful as said lubricant.

DISCLOSURE OF THE INVENTION

The invention provides a fluorine-containing polyether compound represented by formula (1) or (1')

or

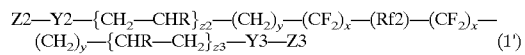

wherein Rf1 and Rf2 are the same or different and each represents a fluorine-containing polyether group, a perfluoroalkyl group or a perfluoroalkenyl group; Y1, Y2 and Y3 are the same or different and each represents a single bond, —O—, —COO— or —CONH—; Rs are the same or different and each represents a hydrogen atom or a hydroxyl group provided that Y1, Y2 and Y3 represent —O— when R is a hydroxyl group; Z1, Z2 and Z3 are a group containing an organic free radical in structure thereof; x and y are an integer of 0–10, respectively; z1, z2 and z3 are 0 or 1. The invention also provides a lubricant, a lubricant for magnetic recording medium and a magnetic recording medium comprising said fluorine-containing polyether compound.

The fluorine-containing polyether groups represented by Rf1 and Rf2 include groups represented by formulae (2) and (3):

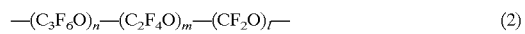

and

wherein with respect to formula (2), l, m and n are 0 or a positive integer, respectively and meet the expression 2<l+m+n<200;
with respect to formula (3), a, b, c, d, e and f are 0 or a positive integer, respectively and meet the expressions 2<a+b+c+d+e+f<200, and, a+c+d+f>1.

Molecular weight of the fluorine-containing polyether compound of the invention is not specifically limited to, but is preferably about 1,000 to about 10,000.

With respect to formula (2), preferable l, m and n are:
l=1–10, m=0, n=10–80;
l=3–80, m=3–80, n=0;
l=m=0, n=10–80.

The following relations are met by l, m and n: 2<l+m+n<200; preferably 5<l+m+n<100; more preferably 10<l+m+n<80.

With respect to formula (3), preferable a, b, c, d, e and f are:
a=0–10; b=0–10; c=0–10; d=1–20; e=0–10; and f=10–80.
Preferably, d=1–10, f=10–80, and a=b=c=e=0.
In addition, 2<a+b+c+d+e+f<200, preferably 10<a+b+c+d+e+f<50.

Perfluoroalkyl groups or perfluoroalkenyl groups represented by Rf1 and Rf2 include groups represented by formula (4):

with respect to formula (4), p is an integer of 2–20; and q is an integer of 2–20.

Preferable p and q are an integer of 1–8, respectively.

Y1, Y2 and Y3 preferably include —O— and —CONH—, more preferably —O—.

x is $0 \leq x \leq 10$, preferably $2 \leq x \leq 4$.

y is $0 \leq y \leq 10$, preferably $0 \leq y \leq 2$.

Z1, Z2 and Z3 represent one selected from the group consisting of groups containing an organic free radical represented by formulae (5) to (7) provided that Tempel is bound at 4-position of a piperidine ring and that DPPH and VD2 are bound at 3- or 4-position of a phenyl group:

(5)

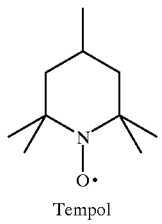

Tempol (6)

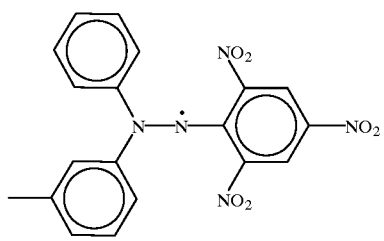

DPPH (7)

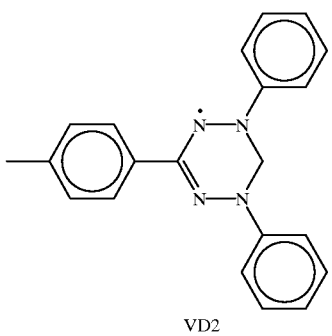

VD2

Preferable organic free radicals include a radical group represented by formula (5).

Said organic radicals are stable and maintain radical state at normal temperature under normal pressure. However, said organic radicals are sensitive to other radicals and tends to be bound to other radicals.

X represents fluorine atom, chlorine atom or hydrogen atom, preferably fluorine atom.

The fluorine-containing polyether compound of the invention includes the following.

(1)

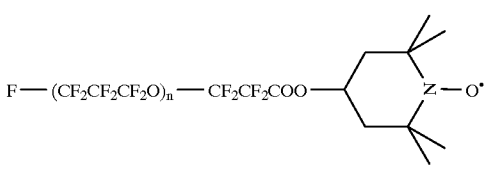

wherein n is an integer of 10–80.

(2)

wherein 20≦d+f≦30, and, d:f=(2 to 3):(8 to 7).
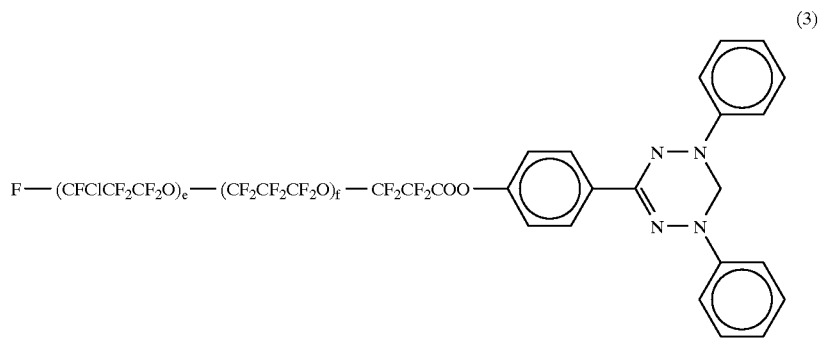
(3)
wherein 19≦e+f≦29, and, e:f=(2 to 3):(8 to 7).
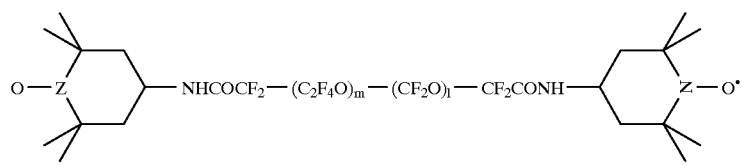
(4)
wherein 9≦m+l≦15, and, m:l=(1 to 5):(5 to 1).
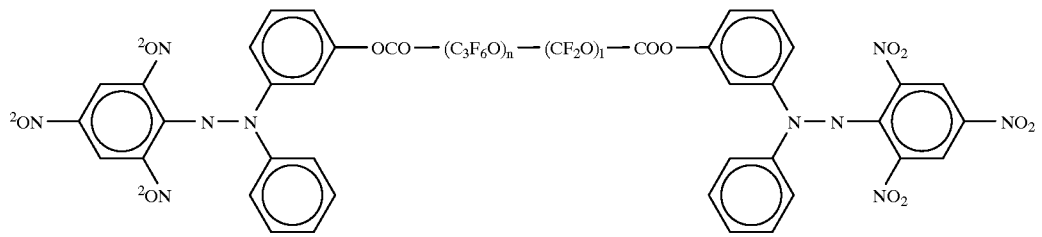
(5)
wherein 3≦n+l≦80, and, n:l=(1 to 50):(2 to 1).
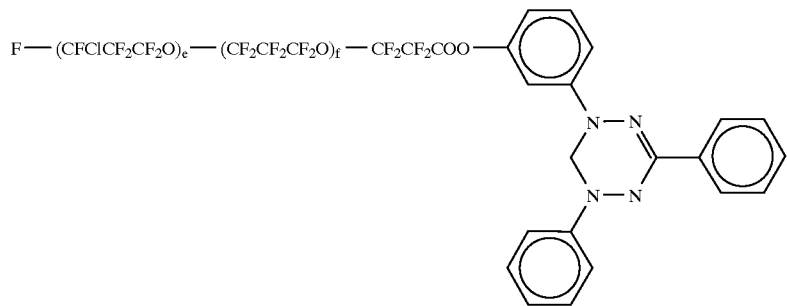
(6)
wherein n is an integer of 5–35.

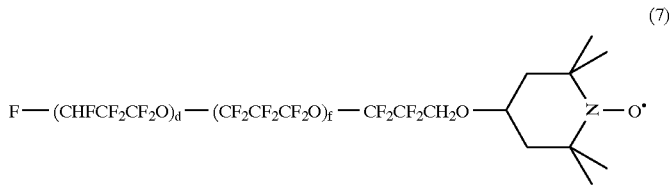
wherein 20≦d+f≦60, and, d:f=(1 to 5):(9 to 5).
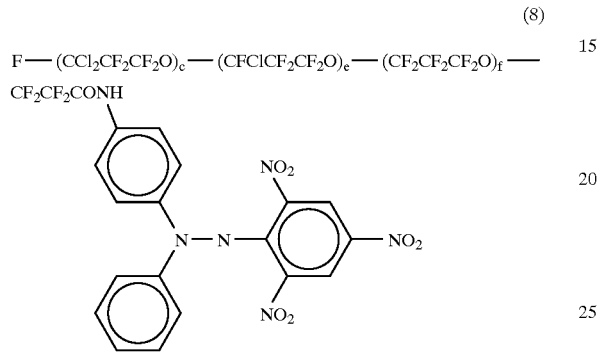
wherein 12≦c+e+f≦100, and c:d:f=(0 to 30):(20 to 50):(50 to 80).
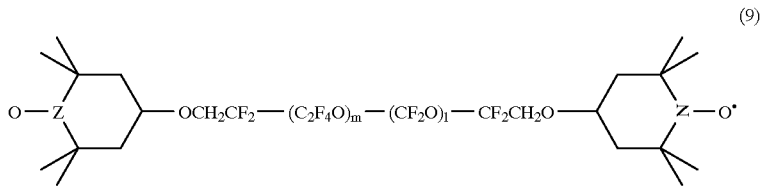
wherein 9≦m+l≦15, and, m:l=(1 to 5):(2 to 1).
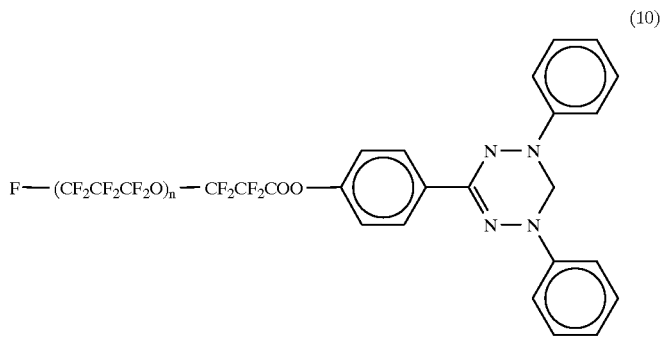
wherein n is an integer of 7–35.

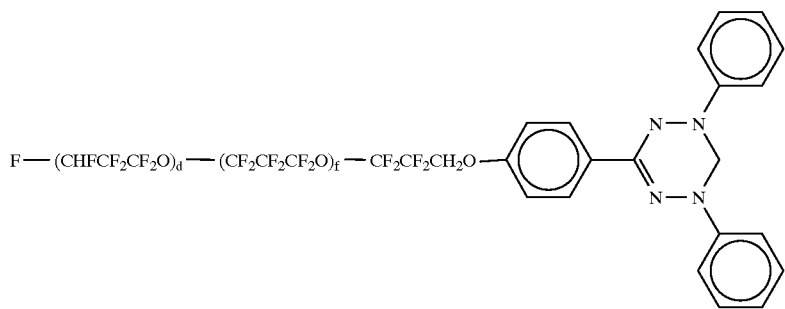
(11)
wherein $10 \leq d+f \leq 30$, and, $d:f=(1 \text{ to } 3):(9 \text{ to } 7)$.
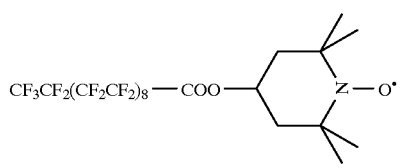
(12)
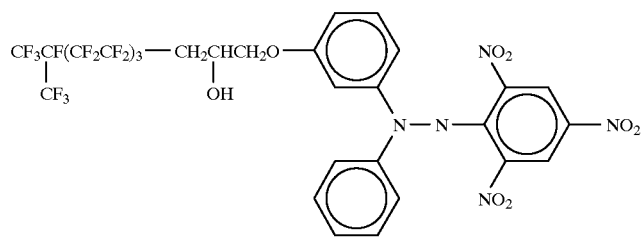
(13)
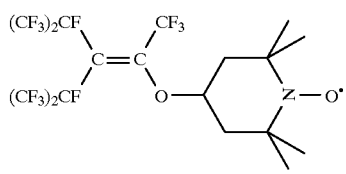
(14)
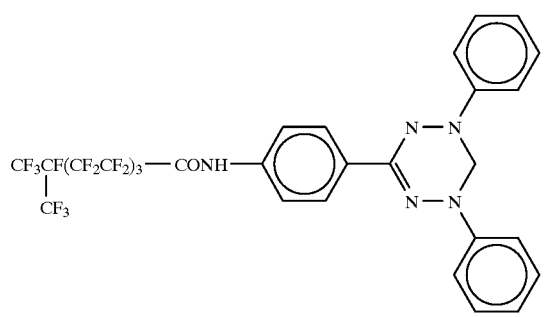
(15)
The fluorinated compounds may be produced according to the following reaction formulae.

<Reaction formula 1>

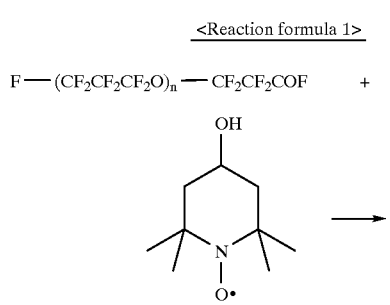

wherein n is as defined above.

<Reaction formula 2>

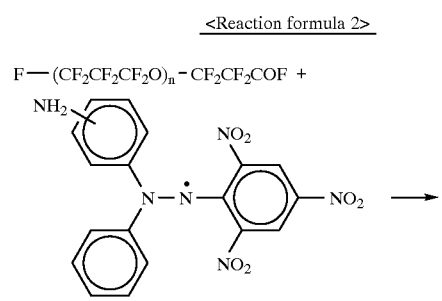

wherein n is as defined above.

<Reaction formula 3>

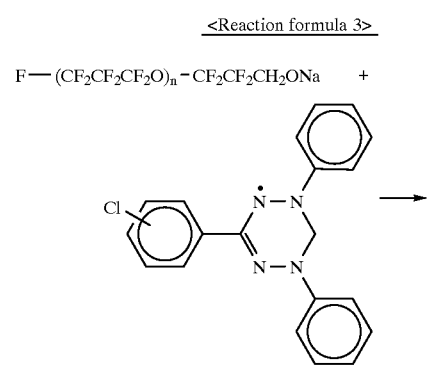

-continued

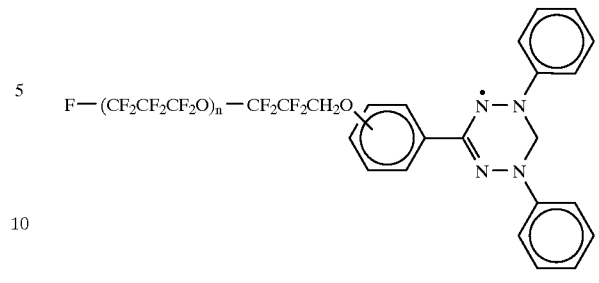

wherein n is as defined above.

<Reaction formula 4>

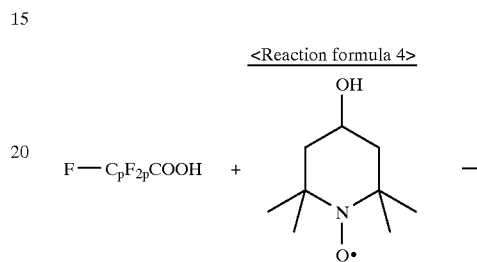

wherein p is as defined above.

<Reaction formula 5>

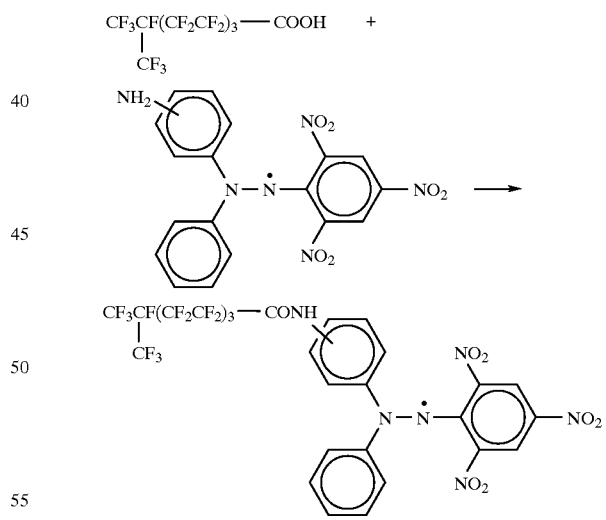

Reaction Formula 1

The desired ester is obtained by reacting an acid fluoride with an alcohol in the presence of a base. The reaction may be carried out by using about 1 mole of said alcohol and about 1–2 moles of said base per 1 mole of said acid fluoride at about room temperature for 2–48 hours. The base includes triethylamine and like organic amines. Reaction solvents include chloroform, benzene, fluorinated solvent, etc.

Reaction Formula 2

The desired amide is obtained by reacting an acid fluoride with an amine in the presence of a base. The reaction may be carried out by using about 1 mole of said amine and about 1–2 moles of said base per 1 mole of said acid fluoride at about room temperature for 2–48 hours. The base includes triethylamine and like organic amines. Reaction solvents include chloroform, benzene, fluorinated solvents, etc.

Reaction Formula 3

The desired ether is obtained by reacting a sodium alkoxide with chloro-VDZ. The reaction may be carried out by using about 1 mole of said chloro-VDZ per 1 mole of said sodium alkoxide at about room temperature for 2–48 hours. Reaction solvents include benzene, THF, etc.

Reaction Formula 4

The desired ester is obtained by reacting a straight-chain perfluorocarboxylic acid with 4-hydroxy-Tempol in the presence of a condensing agent. The reaction may be carried out by using about 1 mole of 4-hydroxy-Tempol per 1 mole of said perfluorocarboxylic acid at about room temperature for 2–48 hours. Reaction solvents include benzene, chloroform, fluorinated solvents, etc. The condensing agent includes dicyclohexylcarbodiimide (DCC), etc.

Reaction Formula 5

The desired ester is obtained by reacting a branched perfluorocarboxylic acid with amino-DPPH in the presence of a condensing agent. The reaction may be carried out by using about 1 mole of amino-DPPH per 1 mole of said perfluorocarboxylic acid at about room temperature for 2–48 hours. Reaction solvents include benzene, chloroform, fluorinated solvents, etc. The condensing agent includes dicyclohexylcarbodiimide (DCC), etc.

The compounds of formulae (1) and (1') of the invention may be produced according to the following reaction steps.

<Reaction step I>

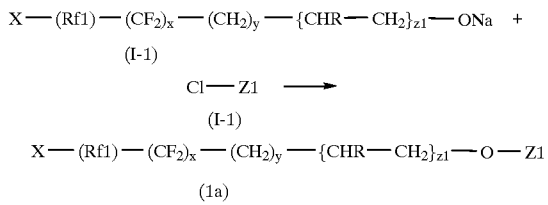

wherein X, x, y, Rf1, Z1 and z1 are as defined above; R represents a hydrogen atom.

The desired ether compound (1a) is obtained by reacting a sodium alkoxide of formula (I-1) with a chlorine-containing compound of formula (I-2) in the presence of a solvent. The reaction may be carried out by using about 1–1.5 moles of the chlorine-containing compound of formula (I-2) per 1 mole of the sodium alkoxide of formula (I-1) at about room temperature to boiling point of the solvent for about 2–48 hours. The solvent includes benzene, toluene and like aromatic hydrocarbons, ether, tetrahydrofuran and like ethers, fluorinated solvents, etc.

<Reaction step I'>

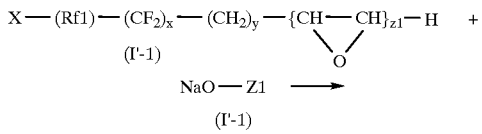

-continued $$X-(Rf1)-(CF_2)_x-(CH_2)_y-\{CHR-CH_2\}_{z1}-O-Z1$$

(1a')

wherein X, x, y, Rf1 and Z1 are as defined above; R represents a hydroxyl group; z1 is 1.

The desired ether compound (1'a) is obtained by reacting an epoxide of formula (I'-1) with a sodium alkoxide of formula (I'-2) in the presence of a solvent. The reaction may be carried out by using about 1–1.5 moles of said sodium alkoxide of formula (I'-2) per 1 mole of said epoxide of formula (I'-1) at about room temperature to boiling point of the solvent for about 2–48 hours. The solvent includes benzene, toluene and like aromatic hydrocarbons, ether, tetrahydrofuran and like ethers, fluorinated solvents, etc.

<Reaction step II>

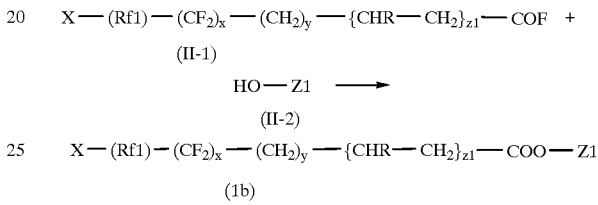

wherein R, X, x, y, Rf1, Z1 and z1 are as defined above.

The desired ester compound (1b) is obtained by reacting an acid fluoride of formula (II-1) with an alcohol of formula (II-2) in the presence or absence of a solvent and base. The reaction may be carried out by using about 1–1.5 moles of the alcohol of formula (II-2), and about 1–2 moles of the base when employed per 1 mole of said acid fluoride of formula (II-1) at about room temperature to 100° C. for about 2–48 hours. Said base includes triethylamine, dimethylaminopyridine and like tertiary amines. The solvent includes benzene, toluene and like aromatic hydrocarbons, chloroform, dichloromethane and like halogenated hydrocarbons, fluorinated solvent, etc.

<Reaction step III>

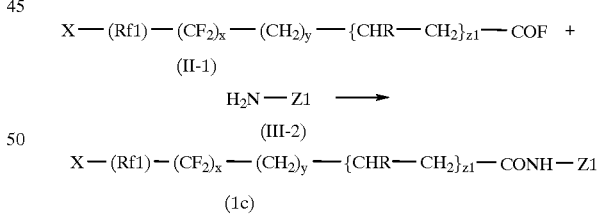

wherein X, x, y, Rf1, z1 and Z1 are as defined above; R represents a hydrogen atom.

The desired amide compound (1c) is obtained by reacting the acid fluoride of formula (II-1) with an amine of formula (III-2) in the presence or absence of a solvent and base. The reaction may be carried out by using about 1–1.5 moles of the amine of formula (III-2) per 1 mole of said acid fluoride of formula (II-1) at about room temperature to 100° C. for about 2–48 hours. Said base includes triethylamine, dimethylaminopyridine and like tertiary amines. The solvent includes benzene, toluene and like aromatic hydrocarbons, chloroform, dichloromethane and like halogenated hydrocarbons, fluorinated solvents, etc.

A method for producing the compound of formula (1') is shown below.

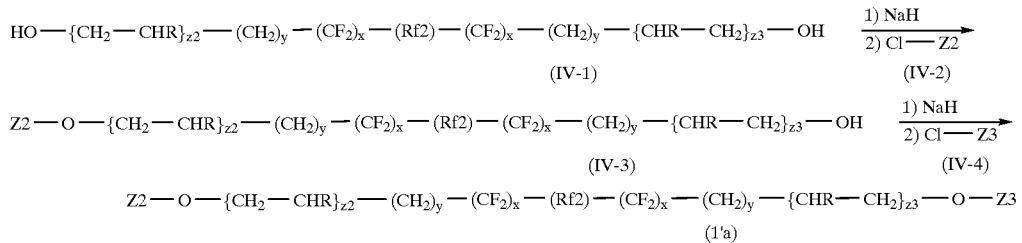

wherein x, y, Rf2, Z2, Z3, z2 and z3 are as defined above; R represents a hydrogen atom.

The mono-ether compound (IV-3) is obtained by reacting a glycol of formula (IV-1) with sodium hydride and a halogenated compound of formula (IV-2) in the presence of a solvent. The reaction may be carried out by using about 1 mole of sodium hydride and about 1 mole of said halogenated compound of formula (IV-2) per 1 mole of said glycol of formula (IV-1) at about room temperature to 100° C. for about 2–48 hours. The solvent includes benzene, toluene and like aromatic hydrocarbons, ether, tetrahydrofuran and like ethers, fluorinated solvents, etc.

The desired compound (1'a) is obtained by reacting the mono-ether compound of formula (IV-3) with sodium hydride and a halogenated compound of formula (IV-4) under the same conditions as above.

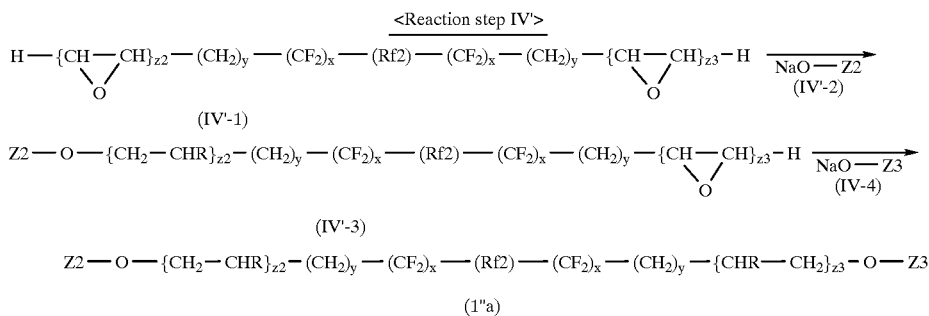

wherein x, y, Rf2, Z2, Z3, z2 and z3 are as defined above; R represents a hydroxyl group.

The compound of formula (IV'-3) is obtained by reacting 1 mole of a diepoxide of formula (IV-1) with about 1 mole of a sodium alkoxide of formula (IV'-2) in the presence of a solvent. The compound of formula (1"a) is then obtained by reacting 1 mole of the compound of formula (IV'-3) with about 1 mole of the sodium alkoxide of formula (IV-4). The reaction is conducted under the same conditions as <Reaction step I'>.

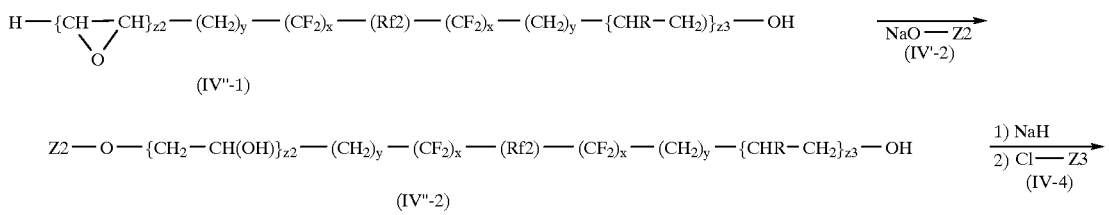

-continued

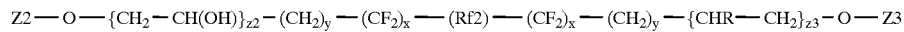

(1″a)

wherein x, y, Rf2, Z2, Z3 and z3 are as defined above; R represents a hydroxyl group; z2 is 1.

The compound of formula (IV″-2) is obtained by reacting 1 mole of the mono-epoxide of formula (IV′-1) with about 1 mole of the sodium alkoxide of formula (IV′-2) in the presence of a solvent. The compound of formula (1′″a) is then obtained by reacting 1 mole of the compound of formula (IV″-2) with about 1 mole of NaH and about 1 mole of the compound of formula (IV-4). The first epoxy-opening reaction is conducted according to the procedure of <Reaction step I′> and the following ether-forming reaction is conducted according to the procedure of <Reaction step IV>.

<Reaction step V>

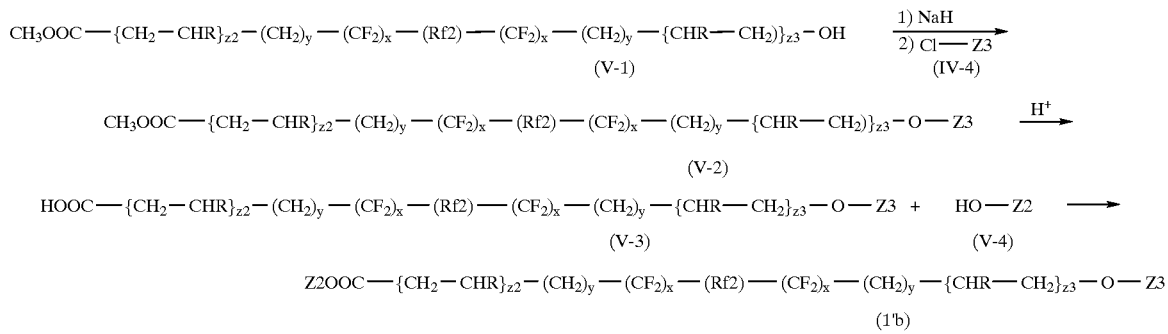

wherein R, x, y, Rf2, Z2, Z3, z2 and z3 are as defined above.

The mono-ether of formula (V-2) is obtained by reacting a compound of formula (V-1) with sodium hydride and the halogenated compound of formula (IV-4) in the presence of a solvent under the same conditions as <Reaction step IV>. The carboxylic acid of formula (V-3) is then obtained by reacting said mono-ether (V-2) with a catalytic or excessive amount of an acid such as diluted HCl or diluted sulfuric acid at about room temperature to boiling point of said solvent for 2 to 72 hours. Said solvent includes water and aqueous organic solvents. The organic solvents include acetone, ethanol, methanol and like alcohols, DMF, DMSO, THF, etc. The compound of formula (1′b) is obtained by reacting the carboxylic acid of formula (V-3) with an alcohol of formula (V-4) in the presence of a condensing agent. The condensation reaction is carried out under the same conditions as <Reaction formula 4>.

<Reaction step VI>

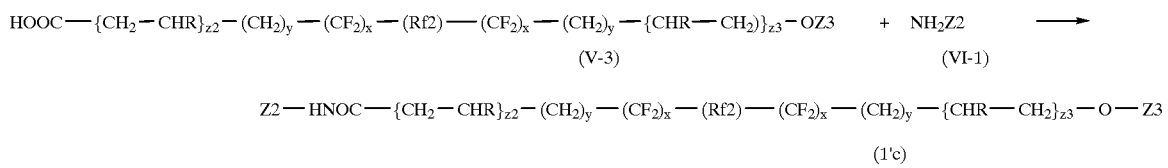

wherein R, x, y, Rf2, Z2, Z3, z2 and z3 are as defined above.

The compound of formula (1'c) is obtained by reacting the carboxylic acid of formula (V-3) with an amine of formula (VI-1) in the presence of a condensing agent, such as DCC. The reaction may be carried out in the same conditions as <Reaction formula 4>.

<Reaction step VII>

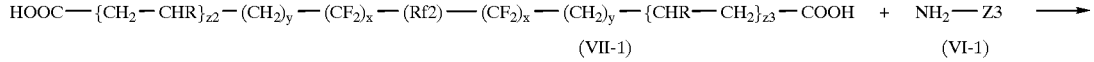
(VII-1) (VI-1)

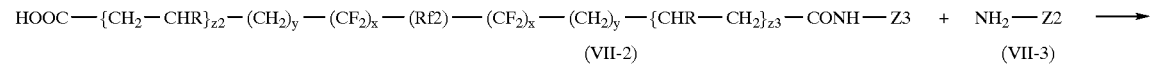
(VII-2) (VII-3)

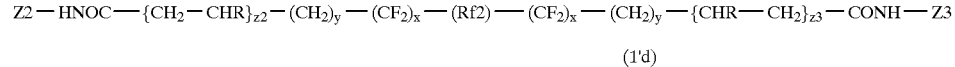
(1'd)

wherein R, x, y, Rf2, Z2, Z3, z2 and z3 are as defined above.

The mono-amide of formula (VII-2) is obtained by reacting a compound of formula (VII-1) with the amine of formula (VI-1) in the presence of a condensing agent. The reaction for preparing mono-amide of formula (VII-2) may be carried out in the same conditions as <Reaction formula 4> by using about 1 mole of amine of formula (VII-3) per 1 mole of the compound of formula (VII-1). Subsequently, the desired diamide of formula (1'd) is obtained by reacting the monoamide of formula (VII-2) with an amine of formula (VII-3) in the presence of a condensing agent. The condensation reaction may be carried out in the same conditions as <Reaction formula 4>.

<Reaction step VIII>

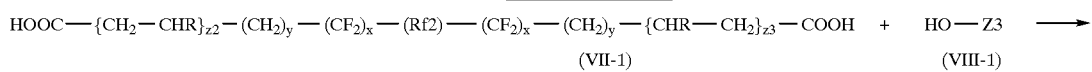
(VII-1) (VIII-1)

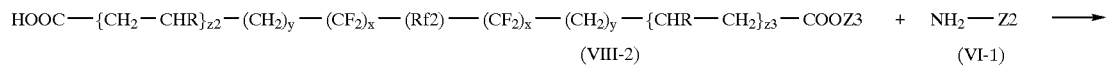
(VIII-2) (VI-1)

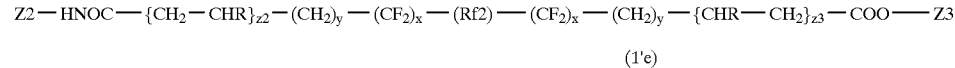
(1'e)

wherein R, x, y, Rf2, Z2, Z3, z2 and z3 are as defined above.

The mono-ester of formula (VIII-2) is obtained by reacting the dicarboxylic acid of formula (VII-1) with an alcohol of formula (VIII-1) in the presence of a condensing agent. The desired monoamide-monoester of formula (1'd) is obtained by reacting the monoester of formula (VIII-2) with the amine of formula (VI-1) in the presence of a condensing agent. Each of condensation reactions may be carried out in the same conditions as <Reaction formula 4>.

<Reaction step IX>

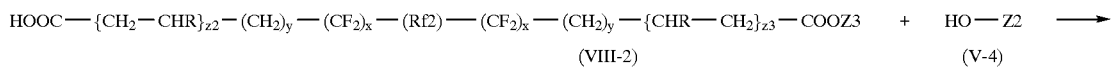
(VIII-2) (V-4)

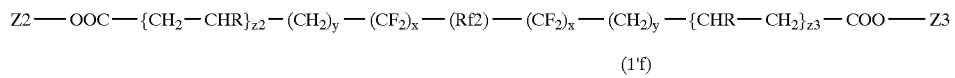
(1'f)

wherein R, x, y, Rf2, Z2, Z3, z2 and z3 are as defined above.

The desired compound of formula (1'f) is obtained by reacting the monoester of formula (VIII-2) with the alcohol of formula (V-4) in the presence of a condensing agent. The condensation reaction may be carried out in the same conditions as <Reaction formula 4>.

<Reaction step X>

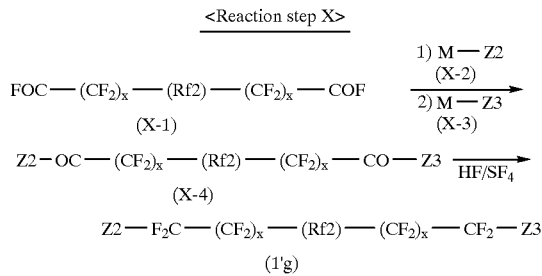

wherein Rf2, Z2 and Z3 are as defined above; x represents an integer of 0–9; M represents Li, Mg or Cu.

The diketone of formula (X-4) is obtained by reacting the di-(acid fluoride) of formula (X-1) obtained from dicarboxylic acid of formula (VII-1) (y=0, x=0–9) with the compound of formula (X-2) and the compound of formula (X-3) in this sequence. The reaction may be carried out under known conditions by using about 1 mole of each of compounds of formulae (X-2) and (X-3) per 1 mole of the di-(acid fluoride) of formula (X-1). The compound of formula (1'g) is obtained by reacting the diketone thus obtained in HF/SF$_4$ under conditions of at 120–180° C. and 20–60 atms for 20–48 hours.

<Reaction step XI>

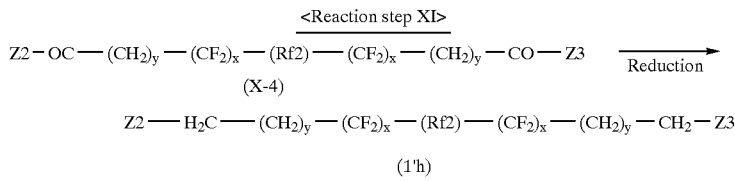

wherein x, Rf2, Z2 and Z3 are as defined above; y represents an integer of 0–9.

The compound of formula (1'h) is obtained by reacting the diketone of formula (X-4) according to known methods for converting ketone into methylene, such as (1) a method of hydrogenation after forming dithioketal, (2) Clemmensen reduction, (3) Wolff-Kishner reduction using hydrazine, etc. <Reaction Step XII> wherein x, y, Rf2, Y3, Z2 and Z3 are as defined above; Y2 represents a single bond.

The desired compound of formula (1'i) is obtained by reacting the compound of formula (XII-1) obtained from the carboxylic acids of formulae (V-3), (VII-2) and (VIII-2) with the compound of formula (X-2) according to known methods to produce the ketone of formula (XII-2), followed by fluorinating or reducing said ketone in the same manner as <Reaction step X> or <Reaction step XI>.

The magnetic recording medium with lubricant of the invention may be obtained by conventional methods, such as spraying a solution of the fluorine-containing compound of the invention dissolved in organic solvent, such as trichlorotrifluoro-ethane, freon-316 etc. on a magnetic body, or dipping a whole of magnetic body in said solution for coating.

According to the invention, fluorine-containing polyether compounds especially useful as lubricant for magnetic recording medium are obtained. The magnetic recording medium to which the fluorine-containing polyether compound is applied demonstrates an excellent durability.

BEST MODE FOR CARRYING OUT THE INVENTION

The invention is described in more detail using examples and comparative examples. The present invention is in no way limited by the examples.

EXAMPLE 1

A 100 g of F—(CF$_2$CF$_2$CF$_2$O)$_n$—CF$_2$CF$_2$COF (average n=25) was dissolved in 200 ml of perfluorohexane. A 20 g of 4-hydroxy-2,2,6,6-tetramethylpiperidine-1-oxide was added to the resulting solution with stirring, and the mixture was heated at 60° C. for 100 hours. The resulting mixture was filtered, and the filtrate was evaporated to obtain 96 g of the desired oily compound shown below:

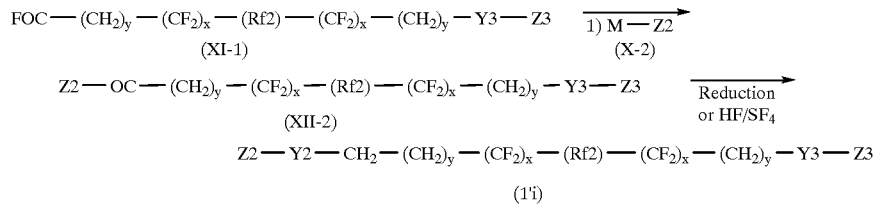

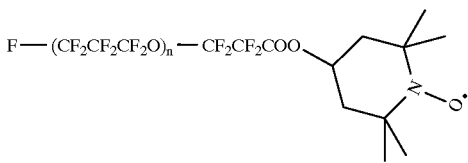

wherein average n is 25.

According to IR analysis of said compound, the absorption at 1890 cm$^{-1}$ corresponding to acid chloride is disappeared and the absorption at 1780 cm$^{-1}$ corresponding to ester occurs.

EXAMPLE 2

| | |
|---|---|
| F—(CHFCF$_2$CF$_2$O)$_d$—(CF$_2$CF$_2$CF$_2$O)$_f$—CF$_2$CF$_2$COF (average d + F = 20; and d:f = 3:7) | 100 g |
| 4-Amino-2,2,6,6-tetramethylpiperidine-1-oxide | 20 g |
| Tetrachlorohexafluorobutane | 100 g |
| Triethylamine | 1 ml |

A mixture of said compounds were refluxed for 60 hours with vigorous stirring. The resulting mixture was allowed to stand for filtration. Tetrachlorohexafluorobutane was removed from the filtrate by evaporation to obtain 98 g of the desired oily compound having the following formula.

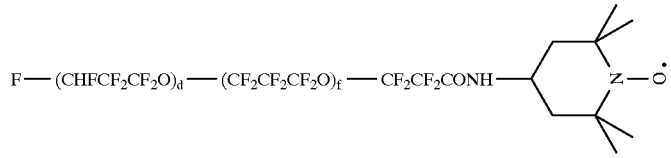

(average d+F=20; and d:f=3:7)

Elemental Analysis

| | | | | |
|---|---|---|---|---|
| Calculated | C: 24.5% | H: 0.7% | F: 64.1% | N: 0.8% |
| Found | C: 24.0% | H: 0.8% | F: 64.8% | N: 0.7% |

According to IR analysis of said compound, the absorption at 1890 cm$^{-1}$ corresponding to acid chloride is disappeared and the absorption at 1790 cm$^{-1}$ corresponding to amide occurs.

EXAMPLE 3

| | |
|---|---|
| F—(CF$_2$CF$_2$CF$_2$O)$_n$—CF$_2$CF$_2$CH$_2$ONa (average n = 25) | 100 g |
| 4-chloro-2,2,6,6-tetramethylpiperidine-1-oxide | 20 g |
| Trichlorotrifluoroethane | 200 g |

A mixture of said compounds were refluxed for 60 hours with vigorous stirring. The resulting mixture was allowed to stand for filtration. Trichlorotrifluoroethane was removed from the filtrate by evaporation to obtain 88 g of the desired oily compound having the following formula.

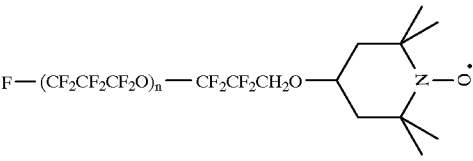

(average n=25)

Elemental Analysis

| | | | | |
|---|---|---|---|---|
| Calculated | C: 23.4% | H: 0.4% | F: 66.1% | N: 0.3% |
| Found | C: 22.9% | H: 0.3% | F: 65.5% | N: 0.2% |

According to IR analysis of said compound, the absorption at 2950 cm$^{-1}$ based on C—H is assigned.

EXAMPLE 4

| | |
|---|---|
| HOOCCF$_2$O—(C$_2$F$_4$O)$_m$—(CF$_2$O)$_l$—CF$_2$COOH (m + l = 12, and m:l = 6:7) | 50 g |
| (4-Hydroxyphenyl)-2-phenyl-1-picrylhydrazine | 15 g |
| Perfluorohexane | 100 g |

A mixture of said compounds were refluxed for 30 hours with vigorous stirring. The resulting mixture was allowed to stand for filtration. Perfluorohexane was removed from the filtrate by evaporation to obtain 29 g of the desired oily compound having the following formula.

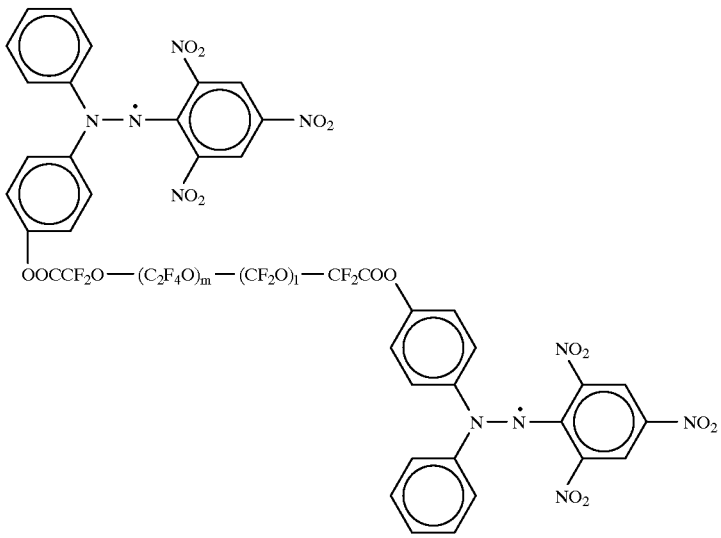

(m+l=12, and, m:l=6:7)

Elemental Analysis

| Calculated | C: 24.7% | H: 1.2% | F: 42.3% | N: 7.4% |
| Found | C: 25.2% | H: 1.3% | F: 42.9% | N: 7.1% |

According to IR analysis of said compound, the absorption in 1500–1600 cm$^{-1}$ based on phenyl groups of DPPH is assigned.

EXAMPLE 5

| CF$_3$CF$_2$(CF$_2$CF$_2$)$_8$—COOH | 100 g |
| 4-Hydroxy-2,2,6,6-tetramethylpiperidine-1-oxide | 40 g |
| Trichlorotrifluoroethane | 200 g |

A mixture of said compounds were refluxed for 24 hours with vigorous stirring. The resulting mixture was allowed to stand for filtration. Perfluorohexane was removed from the filtrate by evaporation to obtain 76 g of the desired oily compound having the following formula.

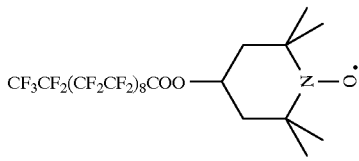

Elemental Analysis

| Calculated | C: 30.1% | H: 1.5% | F: 62.9% | N: 1.3% |
| Found | C: 29.3% | H: 1.3% | F: 64.1% | N: 1.1% |

According to IR analysis of said compound, the absorption in 2900–3000 cm$^{-1}$ based on C—H is assigned.

EXAMPLE 6

A 100 g of 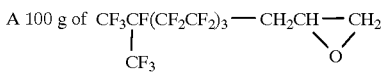

was dissolved in 200 ml of perfluorohexane and stirred in a flask. A 20 g of 4-hydroxy-2,2,6,6-tetramethylpiperidine-1-oxide was added thereto and the resulting mixture was heated at 60° C. for 20 hours. After disappearance of the starting epoxy compound determined by gas chromatography analysis, the reaction mixture was filtered. The filtrate was evaporated for removal of perfluorohexane to obtain 83 g of the desired oily compound shown below:

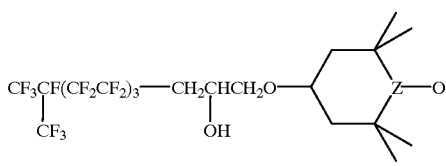

Elemental Analysis

| Calculated | C: 36.1% | H: 3.3% | F: 51.7% | N: 2.0% |
| Found | C: 36.9% | H: 3.5% | F: 50.6% | N: 1.7% |

According to IR analysis of said compound, the absorption around 3300 cm$^{-1}$ based on —OH is assigned.

Fluorine-containing compounds having VDZ may be obtained by using VDZ in place of Tempol and DPPH in said examples 1–6.

EXAMPLE 7

A hard disc having carbon layers as outermost layer was dipped into a lubricant solution consisting of 0.1% by weight of fluorine-containing polyether prepared in example 1 dissolved in perfluorohexane. Lubricant layers were formed on the disc by heat-treatment at 80° C. for 1 hour after taking out the disc from the solution. The lubricant layer was 20 Å in thickness.

The results of duration test of the hard disc using CSS tester shows that coefficient of friction thereof was kept 0.5 or less after 40,000 times of the test.

EXAMPLE 8

A hard disc was treated in the same manner as in example 7 except that the fluorine-containing polyether prepared in example 6 was employed. The lubricant layer was 20 Å in thickness.

The results of duration test of the hard disc using CSS tester shows that coefficient of friction exceeded 0.5 after 16,000 times of the test.

Comparative Example 1

The procedure of example 7 was repeated except that perfluoroether with no organic free radical at terminals, i.e., F—(CF$_2$CF$_2$CF$_2$O)$_{25}$—CF$_2$CF$_3$ was employed. The lubricant layer was 20 Å in thickness.

The results of duration test of the hard disc using CSS tester shows that coefficient of friction exceeded 0.5 after 3,000 times of the test.

We claim:

1. A fluorine-containing polyether compound represented by formula (1) or (1')

X—(Rf1)—(CF$_2$)$_x$—(CH$_2$)$_y$—{CHR—CH$_2$}$_{z1}$—Y1—Z1  (1)

Z2—Y2—{CH$_2$—CHR}$_{z2}$—(CH$_2$)$_y$—(CF$_2$)$_x$—(Rf2)—(CF$_2$)$_x$—(CH$_2$)$_y$—{CHR—CH$_2$}$_{z3}$—Y3—Z3  (1')

wherein Rf1 and Rf2 are the same or different and each represents a fluorine-containing polyether group, a perfluoroalkyl group or a perfluoroalkenyl group represented by formula (2), (3) or (4):

—(C$_3$F$_6$O)$_n$—(C$_2$F$_4$O)$_m$—(CF$_2$O)$_l$—  (2);

or

—(CH$_2$CF$_2$CF$_2$O)$_a$—(CHClCF$_2$CF$_2$O)$_b$—(CCl$_2$CF$_2$CF$_2$O)$_c$—(CHFCF$_2$CF$_2$O)$_d$—(CFClCF$_2$CF$_2$O)$_e$—(CF$_2$CF$_2$CF$_2$O)$_f$—;  (3)

wherein with respect to formula (2), l, m and n are 0 or a positive integer, respectively and meet the expression 2<l+m+n<200;

with respect to formula (3), a, b, c, d, e and f are 0 or a positive integer respectively and meet the expressions 2<a+b+c+d+e+f<200, and a+c+d+f>1; and;

Y1, Y2 and Y3 are the same or different and each represents a single bond, —O—, —COO— or —CONH—; x and y are an integer of 0–10 respectively; z1, z2 and z3 are the same or different and are 0 or 1, respectively; Rs are the same or different and each represents a hydrogen atom or a hydroxyl group provided that Y1, Y2 and Y3 represent —O— when Rs represent a hydroxyl group); Z1, Z2 and Z3 are any one group selected from the group consisting of organic free radicals represented by formulae (5) to (7):

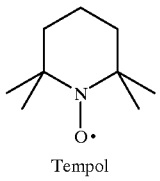

Tempol (5)

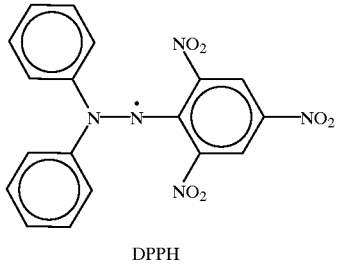

DPPH (6)

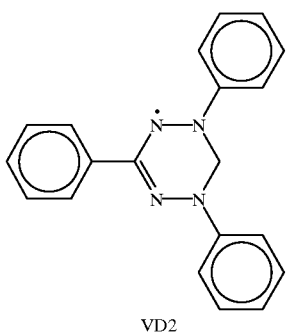

VD2

(7)

provided that Tempel is bound at 4-position of a piperidine ring and that DPPH and VD2 are bound at 3- or 4-position of a phenyl group; X represents a hydrogen atom, fluorine atom or chlorine atom.

2. A compound as defined in claim 1 wherein Rf1 and Rf2 are the same or different and each is a fluorine-containing polyether group represented by formula (2):

—(C$_3$F$_6$O)$_n$—(C$_2$F$_4$O)$_m$—(CF$_2$O)$_l$—  (2)

wherein l, m and n are O or a positive integer, respectively and meet the expression 2<l+m+n<200.

3. A compound as defined in claim 1 wherein Rf1 and Rf2 are the same or different and each is a fluorine-containing polyether group represented by formula (3):

—(CH$_2$CF$_2$CF$_2$O)$_a$—(CHClCF$_2$CF$_2$O)$_b$—(CCl$_2$CF$_2$CF$_2$O)$_c$—(CHFCF$_2$CF$_2$O)$_d$—(CFClCF$_2$CF$_2$O)$_e$—(CF$_2$CF$_2$CF$_2$O)$_f$—  (3)

wherein a, b, c, d, e and f are O or a positive integer respectively and meet the expressions 2<a+b+c+d+e+f<200, and a+c+d+f>1.

4. A magnetic recording medium comprising a magnetic body having applied thereto the compound of claim 1 as a lubricant.

* * * * *